US006790605B1

(12) United States Patent
Short

(10) Patent No.: US 6,790,605 B1
(45) Date of Patent: Sep. 14, 2004

(54) METHODS FOR OBTAINING A DESIRED BIOACTIVITY OR BIOMOLECULE USING DNA LIBRARIES FROM AN ENVIRONMENTAL SOURCE

(75) Inventor: Jay M. Short, Encinitas, CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/375,605

(22) Filed: Aug. 17, 1999

Related U.S. Application Data

(63) Continuation of application No. 08/651,568, filed on May 22, 1996, now Pat. No. 5,939,250.
(60) Provisional application No. 60/008,316, filed on Dec. 7, 1995.

(51) Int. Cl.[7] .................................................. C12Q 1/00
(52) U.S. Cl. ................................ 435/4; 435/6; 435/14; 435/15; 435/16; 435/18; 435/19; 435/21; 435/22; 435/23; 435/24
(58) Field of Search ......................... 435/4, 6, 14, 15, 435/16, 18, 19, 21, 22, 23, 24, 183

(56) References Cited

U.S. PATENT DOCUMENTS

| | | | | |
|---|---|---|---|---|
| 5,316,935 A | * | 5/1994 | Arnold et al. | |
| 5,352,778 A | | 10/1994 | Comb et al. | ............... 536/23.2 |
| 5,500,363 A | * | 3/1996 | Comb et al. | ............... 435/194 |
| 5,605,793 A | * | 2/1997 | Stemmer | ...................... 435/6 |
| 5,811,238 A | | 9/1998 | Stemmer et al. | ............... 435/6 |
| 5,824,485 A | * | 10/1998 | Thompson et al. | ............. 436/6 |
| 5,830,721 A | | 11/1998 | Stemmer et al. | ......... 435/172.1 |
| 5,849,491 A | | 12/1998 | Radomski et al. | ............. 435/6 |
| 5,939,250 A | * | 8/1999 | Short | |

FOREIGN PATENT DOCUMENTS

| | | |
|---|---|---|
| WO | WO 91/16427 | 10/1991 |
| WO | WO 01/30998 A1 | 5/2001 |
| WO | WO 01/31035 A2 | 5/2001 |
| WO | WO 01/31049 A2 | 5/2001 |
| WO | WO 01/42455 A1 | 6/2001 |

OTHER PUBLICATIONS

Arkin et al. "An algorithm for protein engineering: . . . " Proc. Natl. Acad. Sci. U. S. A. 89, 7811–7815, Aug. 1992.*
Delagrave et al. "Searching sequence space to engineer proteins: exponential ensemble mutagenesis" Bio/Technol. 11, 1548–1552, Dec. 1993.*
Stemmer "DNA shuffling by randum fragmentation and assembly: . . . " Proc. Natl. Acad. Sci. U. S. A. 91, 10747–10751, Oct. 1994.*
Osuna et al. "Combinatorial mutagensis of three major groove–contacting residues of EcoRI: . . . " Gene 106, 7–12, 1991.*
Dube et al. Artifical mutant generated by the insertion of random oligonucleotides into the putative . . . Biochemistry 30, 11760–11767, 1991.*
Zhou, Y. et al. (1991) "Random mutagenesis of gene–sized DNA molecules by use of PCR with Taq DNA polymerase" Nucleic Acids Research, vol. 19, No. 21, p. 6052, Nov. 1991.*
Kirshtein, J.D. et al. (1991) "Amplification, cloning, and sequencing of a nifH segment from aquatic microorganisms and natural communities" Applied and Environmental Microbiology, vol. 57, No. 9, pp. 2645–2650, Sep. 1991.*
Ueda, T. et al. (1995) "Remarkable N2–fixing bacterial diversity detected in rice roots by molecular evolution analysis of nifH gene sequences" Journal of Bacteriology, vol. 177, No. 5, pp. 1414–1417, Mar. 1995.*
Hennecke, H. et al. (1985) "Concurrent evolution of nitrogenase genes and 16S rRNA in Rhizobium species and other nitrogen fixing bacteria" Archives of Microbiology, vol. 142, pp. 342–348, 1985.*
Stein and Felbeck, "Kinetic and physical properties of a recombinant RuBisCO from a chemoautotrophic endosymbiont," *Molecular Marine Biology and Biotechnology* 2(5):280–290 (1993).

* cited by examiner

Primary Examiner—Nashaat T. Nashed

(57) ABSTRACT

Disclosed is a process for obtaining an enzyme having a specified enzyme activity derived from a heterogeneous DNA population by screening, for the specified enzyme activity, a library of clones containing DNA from the heterogeneous DNA population which have been exposed to directed mutagenesis towards production of the specified enzyme activity. Also disclosed is a process for obtaining an enzyme having a specified enzyme activity by screening, for the specified enzyme activity, a library of clones containing DNA from a pool of DNA populations which have been exposed to directed mutagenesis in an attempt to produce in the library of clones DNA encoding an enzyme having one or more desired characteristics which can be the same or different from the specified enzyme activity.

21 Claims, No Drawings

METHODS FOR OBTAINING A DESIRED BIOACTIVITY OR BIOMOLECULE USING DNA LIBRARIES FROM AN ENVIRONMENTAL SOURCE

This application claims benefit of U.S. Provisional Application No. 60/008,316, filed Dec. 7, 1995, and is a continuation of U.S. Ser. No. 08/651,568, filed May 22, 1996, now issued as U.S. Pat. No. 5,939,250.

This invention relates to the field of protein engineering. More particularly, the invention relates to the directed mutagenesis of DNA and screening of clones containing the mutagenized DNA for resultant specified protein, particularly enzyme, activity(ies) of interest.

In one aspect the invention provides a process for obtaining an enzyme having a specified enzyme activity derived from a heterogeneous DNA population, which process comprises: screening, for the specified enzyme activity, a library of clones containing DNA from the heterogeneous DNA population which have been exposed to directed mutagenesis towards production of the specified enzyme activity.

Another aspect of the invention provides a process for obtaining an enzyme having a specified enzyme activity, which process comprises: screening, for the specified enzyme activity, a library of clones containing DNA from a pool of DNA populations which have been exposed to directed mutagenesis in an attempt to produce in the library of clones DNA encoding an enzyme having one or more desired characteristics, which can be the same or different from the specified enzyme activity. In a preferred embodiment, the DNA pool which is subjected to directed mutagenesis is a pool of DNA which has been selected to encode enzymes having at least one enzyme characteristic, in particular at least one common enzyme activity.

Also provided is a process for obtaining a protein having a specified activity derived from a heterogeneous population of gene clusters by screening, for the specified protein activity, a library of clones containing gene clusters from the heterogeneous gene cluster population which have been exposed to directed mutagenesis towards production of specified protein activities of interest.

Also provided is a process of obtaining a gene cluster protein product having a specified activity, by screening, for the specified protein activity, a library of clones containing gene clusters from a pool of gene cluster populations which have been exposed to direct mutagenesis to produce in the library of clones gene clusters encoding proteins having one or more desired characteristics, which can be the same or different from the specified protein activity. Preferably, the pool of gene clusters which is subjected to directed mutagenesis is one which has been selected to encode proteins having enzymatic activity in the synthesis of at least one therapeutic, prophylactic or physiological regulatory activity.

The process of either of these aspects can further comprise, prior to the directed mutagenesis, selectively recovering from the heterogeneous population of gene clusters, gene clusters which comprise polycistronic sequences coding for proteins having at least one common physical, chemical or functional characteristic which can be the same or different from the activity observed prior to directed mutagenesis. Preferably, recovering the gene cluster preparation comprises contacting the gene cluster population with a specific binding partner, such as a solid phase-bound hybridization probe, for at least a portion of the gene cluster of interest. The common characteristic of the resultant protein(s) can be classes of the types of activity specified above, i.e., such as a series of enzymes related as parts of a common synthesis pathway or proteins capable of hormonal, signal transduction or inhibition of metabolic pathways or their functions in pathogens and the like. The gene cluster DNA is recovered from clones containing such gene cluster DNA from the heterogeneous gene cluster population which exhibit the activity of interest. Preferably, the directed mutagenesis is site-specific directed mutagenesis. This process can further include a step of pre-screening the library of clones for an activity, which can be the same or different from the specified activity of interest, prior to exposing them to directed mutagenesis. This activity can result, for example, from the expression of a protein or related family of proteins of interest.

The process of any of these aspects can further comprise, prior to said directed mutagenesis, selectively recovering from the heterogeneous DNA population DNA which comprises DNA sequences coding for enzymes having at least one common characteristic, which can be the same or different from the specified enzyme activity. Preferably, recovering the DNA preparation comprises contacting the DNA population with a specific binding partner, such as a solid phase bound hybridization probe, for at least a portion of the coding sequences. The common characteristic can be, for example, a class of enzyme activity, such as hydrolase activity. DNA is recovered from clones containing DNA from the heterogeneous DNA population which exhibit the class of enzyme activity. Preferably, the directed mutagenesis is site-specific directed mutagenesis. The process of this aspect can further include a step of prescreening the library of clones for an activity, which can be the same or different from the specified enzyme activity, prior to exposing them to directed mutagenesis. This activity can result, for example, from the expression of a protein of interest.

The heterogeneous DNA population from which the DNA library is derived is a complex mixture of DNA, such as is obtained, for example, from an environmental sample. Such samples can contain unculturable or uncultured multiple or single organisms. These environmental samples can be obtained from, for example, Arctic and Antarctic ice, water or permafrost sources, materials of volcanic origin, materials from soil or plant sources in tropical areas, etc. A variety of known techniques can be applied to enrich the environmental sample for organisms of interest, including differential culturing, sedimentation gradient, affinity matrices, capillary electrophoresis, optical tweezers and fluorescence activated cell sorting. The samples can also be cultures of a single organism.

The microorganisms from which the libraries may be prepared include prokaryotic microorganisms, such as Eubacteria and Archaebacteria, and lower eukaryotic microorganisms such as fungi, some algae and protozoa. The microorganisms are uncultured microorganisms obtained from environmental samples and such microorganisms may be extremophiles, such as thermophiles, hyperthermophiles, psychrophiles, psychrotrophs, etc.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where a duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produce by polyketide synthases) are valuable as therapeutic agents. Polyketide synthases are multifunctional enzymes that catalyze the biosynthesis of a hugh variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides and postpolyketide biosynthesis genes for generation of novel polyketides for study is appealing. The method(s) of the present invention make it possible to and facilitate the cloning of novel polyketide synthases, since one can generate gene banks with clones containing large inserts (especially when using the f-factor based vectors), which facilitates cloning of gene clusters.

Preferably, the gene cluster DNA is ligated into a vector, particularly wherein a vector further comprises expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large DNA fragments, such as gene clusters from mixed microbial samples.

The DNA can then be isolated by available techniques that are described in the literature. The IsoQuick® nucleic acid extraction kit (MicroProbe Corporation) is suitable for this purpose.

The term "derived" or "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The DNA isolated or derived from these microorganisms can preferably be inserted into a vector prior to probing for selected DNA. Such vectors are preferably those containing expression regulatory sequences, including promoters, enhancers and the like. Such polynucleotides can be part of a vector and or a composition and still be isolated, in that such vector or composition is not part of its natural environment. Particularly preferred phage or plasmid and methods for introduction and packaging into them are described in detail in the protocol set forth herein.

The following outlines a general procedure for producing gene libraries from both culturable and nonculturable organisms.

Obtain Biomass

DNA Isolation

Shear DNA (25 gauge needle)

Blunt DNA (Mung Bean Nuclease)

Methylate (EcoR I Methylase)

Ligate to EcoR I linkers (GGAATTCC)

Cut back linkers (EcoR I Restriction Endonuclease)

Size Fractionate (Sucrose Gradient)

Ligate to lambda vector (Lambda ZAP® II and gt11)

Package (in vitro lambda packaging extract)

Plate on *E. coli* host and amplify

Clones having an enzyme activity of interest are identified by screening. This screening can be done either by hybridization, to identify the presence of DNA coding for the enzyme of interest or by detection of the enzymatic activity of interest.

The probe DNA used for selectively recovering DNA of interest from the DNA derived from the at least one uncultured microorganism can be a full-length coding region sequence or a partial coding region sequence of DNA for an enzyme of known activity, a phylogenetic marker or other identified DNA sequence. The original DNA library can be preferably probed using mixtures of probes comprising at least a portion of the DNA sequence encoding the specified activity. These probes or probe libraries are preferably single-stranded and the microbial DNA which is probed has preferably been converted into single-stranded form. The probes that are particularly suitable are those derived from DNA encoding enzymes having an activity similar or identical to the specified enzyme activity which is to be screened.

The probe DNA should be at least about 10 bases and preferably at least 15 bases. In one embodiment, the entire coding region may be employed as a probe. Conditions for the hybridization in which DNA is selectively isolated by the use of at least one DNA probe will be designed to provide a hybridization stringency of at least about 50% sequence identity, more particularly a stringency providing for a sequence identity of at least about 75%.

Hybridization techniques for probing a microbial DNA library to isolate DNA of potential interest are well known in the art and any of those which are described in the literature are suitable for use herein, particularly those which use a solid phase-bound, directly or indirectly bound, probe DNA for ease in separation from the remainder of the DNA derived from the microorganisms.

Preferably the probe DNA is "labeled" with one partner of a specific binding pair (i.e. a ligand) and the other partner of the pair is bound to a solid matrix to provide ease of separation of target from its source. The ligand and specific binding partner can be selected from, in either orientation, the following: (1) an antigen or hapten and an antibody or specific binding fragment thereof; (2) biotin or iminobiotin and avidin or streptavidin; (3) a sugar and a lectin specific therefor; (4) an enzyme and an inhibitor therefor; (5) an apoenzyme and cofactor; (6) complementary homopolymeric oligonucleotides; and (7) a hormone and a receptor therefor. The solid phase is preferably selected from: (1) a glass or polymeric surface; (2) a packed column of polymeric beads; and (3) magnetic or paramagnetic particles.

The library of clones prepared as described above can be screened directly for enzymatic activity without the need for culture expansion, amplification or other supplementary procedures. However, in one preferred embodiment, it is considered desirable to amplify the DNA recovered from the individual clones such as by PCR.

Further, it is optional but desirable to perform an amplification of the target DNA that has been isolated. In this embodiment the selectively isolated DNA is separated from the probe DNA after isolation. It is then amplified before being used to transform hosts. The double stranded DNA selected to include as at least a portion thereof a predetermined DNA sequence can be rendered single stranded, subjected to amplification and reannealed to provide amplified numbers of selected double stranded DNA. Numerous amplification methodologies are now well known in the art.

The selected DNA is then used for preparing a library for screening by transforming a suitable organism. Hosts, particularly those specifically identified herein as preferred, are transformed by artificial introduction of the vectors containing the target DNA by inoculation under conditions conducive for such transformation.

The resultant libraries of transformed clones are then screened for clones which display activity for the enzyme of interest in a phenotypic assay for enzyme activity.

Having prepared a multiplicity of clones from DNA selectively isolated from an organism, organism, such clones are screened for a specific enzyme activity and to identify the clones having the specified enzyme characteristics.

The screening for enzyme activity may be effected on individual expression clones or may be initially effected on a mixture of expression clones to ascertain whether or not the mixture has one or more specified enzyme activities. If the mixture has a specified enzyme activity, then the individual clones may be rescreened for such enzyme activity or for a more specific activity. Thus, for example, if a clone mixture has hydrolase activity, then the individual clones may be recovered and screened to determine which of such clones has hydrolase activity.

The DNA derived from a microorganism(s) is preferably inserted into an appropriate vector (generally a vector containing suitable regulatory sequences for effecting expression) prior to subjecting such DNA to a selection procedure to select and isolate therefrom DNA which hybridizes to DNA derived from DNA encoding an enzyme (s) having the specified enzyme activity.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9 (Qiagen), psiX174, pBluescript® SK, pBluescript® KS(Stratagene); pTRC99a, pKK223-3, pDR540, pRIT2T (Pharmacia); Eukaryotic: pWLNEO, pXT1, pSG5 (Stratagene) pSVK3, pBPV, pMSG, pSVLSV40 (Pharmacia). Any other plasmid or vector may be used as long as they are replicable and viable in the host.

Another type of vector for use in the: present invention contains an f-factor origin of replication. The f-factor (or fertility factor) in $E.$ $coli$ is a plasmid which effects high frequency transfer of itself during conjugation and less frequent transfer of the bacterial chromosome itself. A particularly preferred embodiment is to use cloning vectors, referred to as a "fosmids," or bacterial artificial chromosome (BAC) vectors. These are derived from the $E.$ $coli$ f-factor which is able to stably integrate large segments of genomic DNA. When integrated with DNA from a mixed uncultured environmental sample, this makes it possible to achieve large genomic fragments in the form of a stable "environmental DNA library."

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ Generally, recombinant expression vectors will include origins of replication and selectable markers permitting transformation of the host cell, e.g., the ampicillin resistance gene of $E.$ $coli$ and $S.$ $cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by trarsformation, calcium phosphate transfection, DEAE-Dextran mediated tansfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature,. pH and the like, are those previously used with the host cell selected for expression, and will be apparent to the ordinarily skilled artisan.

The library may be screened for a specified enzyme activity by procedures known in the art. For example, the enzyme activity may be screened for one or more of the six IUB classes; oxidoreductases, transferases, hydrolases, lyases, isomerases and ligases. The recombinant enzymes which are determined to be positive for one or more of the IUB classes may then be rescreened for a more specific enzyme activity.

Alternatively, the library may be screened for a more specialized enzyme activity. For example, instead of generically screening for hydrolase activity, the library may be screened for a more specialized activity, i.e. the type of bond on which the hydrolase acts. Thus, for example, the library may be screened to ascertain those hydrolases which act on one or more specified chemical functionalities, such as: (a) amide (peptide bonds), i.e. proteases; (b) ester bonds, i.e. esterases and lipases; (c) acetals, i.e., glycosidases etc.

Clones found to have the enzymatic activity for which the screen was performed are sequenced and then subjected to directed mutagenesis to develop new enzymes with desired activities or to develop modified enzymes with particularly desired properties that are absent or less pronounced in the wild-type enzyme, such as stability to heat or organic solvents. Any of the known techniques for directed mutagenesis are applicable to the invention. For example, particularly preferred mutagenesis techniques for use in accordance with the invention include those discussed below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1992).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994).

The term "in vivo mutagenesis" refers to a process of generating random mutations in any cloned DNA of interest which involves the propagation of the DNA in a strain of *E coli* that carries mutations in one or more of the DNA repair pathways. These "mutator" strains have a higher random mutation rate than that of a wild-type parent. Propogating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed: to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, USA, 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C., Biotechnology Research, 11:1548–1552 (1993); and random and site-directed mutagenesis, Arnold, F. H., Current Opinion in Biotechnology, 4:450–455 (1993). All of the references mentioned above are hereby incorporated by reference in their entirety.

EXAMPLE 1

Preparation of a Mammalian DNA Library

The following outlines the procedures used to generate a gene library from a sample of the exterior surface of a whale bone found at 1240 meters depth in the Santa Catalina Basin during a dive expedition.

Isolate DNA.

IsoQuick Procedure as per manufacturer's instructions.

Shear DNA

1. Vigorously push and pull DNA through a 25G double-hub needle and 1-cc syringes about 500 times.
2. Check a small amount (0.5 µg) on a 0.8% agarose gel to make sure the majority of the DNA is in the desired size range (about 3–6 kb).

Blunt DNA

1. Add:

| | |
|---|---|
| $H_2O$ | to a final volume of 405 µl |
| 45 µl | 10× Mung Bean Buffer |
| 2.0 µl | Mung Bean Nuclease (150 u/µl) |

2. Incubate 37° C., 15 minutes.
3. Phenol/chloroform extract once.
4. Chloroform extract once.
5. Add 1 ml ice cold ethanol to precipitate.
6. Place on ice for 10 minutes.
7. Spin in microfuge, high speed, 30 minutes.
8. Wash with 1 ml 70% ethanol.
9. Spin in microfuge, high speed, 10 minutes and dry.

Methylate DNA

1. Gently resuspend DNA in 26 µl TE.
2. Add:

| | |
|---|---|
| 4.0 µl | 10× EcoR I Methylase Buffer |
| 0.5 µl | SAM (32 mM) |
| 5.0 µl | EcoR I Methylase (40 u/µl) |

3. Incubate 37°, 1 hour.

Insure Blunt Ends

1. Add to the methylation reaction:

| | |
|---|---|
| 5.0 µl | 100 mM $MgCl_2$ |
| 8.0 µl | dNTP mix (2.5 mM of each dGTP, dATP, dTTP, dCTP) |
| 4.0 µl | Klenow (5 u/µl) |

2. Incubate 12° C., 30 minutes.
3. Add 450 µl 1X STE.
4. Phenol/chloroform extract once.
5. Chloroform extract once.
6. Add 1 ml ice cold ethanol to precipitate and place on ice for 10 minutes.
7. Spin in microfuge, high speed, 30 minutes.
8. Wash with 1 ml 70% ethanol.
9. Spin in microfuige, high speed, 10 minutes and dry.

Linker Ligation

1. Gently resuspend DNA in 7 µl Tris-EDTA (TE).
2. Add:

| | |
|---|---|
| 14 µl | Phosphorylated EcoR I linkers (200 ng/µl) |
| 3.0 µl | 10× Ligation Buffer |
| 3.0 µl | 10 mM rATP |
| 3.0 µl | T4 DNA Ligase (4Wu/µl) |

3. Incubate 4° C., overnight.

EcoR1 Cutback

1. Heat kill ligation reaction 68° C., 10 minutes.
2. Add:

| | |
|---|---|
| 237.9 µl | $H_2O$ |
| 30 µl | 10× EcoR I Buffer |
| 2.1 µl | EcoR I Restriction Enzyme (100 u/µl) |

3. Incubate 37° C., 1.5 hours.
4. Add 1.5 µl 0.5 M EDTA.
5. Place on ice.

Sucrose Gradient (2.2 ml) Size Fractionation

1. Heat sample to 65° C., 10 minutes.
2. Gently load on 2.2 ml 'sucrose gradient.
3. Spin in mini-ultracentrifuge, 45K, 20° C., 4 hours (no brake).
4. Collect fractions by puncturing the bottom of the gradient tube with a 20G needle and allowing the sucrose to flow through the needle. Collect the first 20 drops in a Falcon 2059 tube then collect 10 1-drop fractions (labelled 1–10). Each drop is about 60 µl in volume.
5. Run 5 µl of each fraction on a 0.8% agarose gel to check the size.
6. Pool fractions 1–4 (about 10–1.5 kb) and, in a separate tube, pool fractions 5–7 (about 5–0.5 kb).
7. Add 1 ml ice cold ethanol to precipitate and place on ice for 10 minutes.
8. Spin in microfuge, high speed, 30 minutes.
9. Wash with 1 ml 70% ethanol.
10. Spin in microfuge, high speed, 10 minutes and dry.
11. Resuspend each in 10 µl TE buffer.

Test Ligation to Lambda Arms

1. Plate assay to get an approximate concentration. Spot 0.5 µl of the sample on agarose containing ethidium bromide along with standards (DNA samples of known concentration). View in UV light and estimate concentration compared to the standards. Fraction 1–4 =>1.0 µg/µl. Fraction 5–7=500 ng/µl.
2. Prepare the following ligation reactions (5 µl reactions) and incubate 4° C., overnight:

| Sample | H$_2$O | 10× Ligase Buffer | 10 mM rATP | Lambda arms (gt11 and ZAP) | Insert DNA | T4 DNA Ligase (4 Wu/µ) |
|---|---|---|---|---|---|---|
| Fraction 1–4 | 0.5 µl | 0.5 µl | 0.5 µl | 1.0 µl | 2.0 µl | 0.5 µl |
| Fraction 5–7 | 0.5 µl | 0.5 µl | 0.5 µl | 1.0 µl | 2.0 µl | 0.5 µl |

Test Package and Plate

1. Package the ligation reactions following manufacturer's protocol. Package 2.5 µl per packaging extract (2 extracts per ligation).
2. Stop packaging reactions with 500 µl SM buffer and pool packaging that came from the same ligation.
3. Titer 1.0 µl of each on appropriate host (OD$_{600}$=1.0) [XLI-Blue MRF for ZAP and Y1088 for gt 11]
   Add 200 µl host (in mM MgSO$_4$) to Falcon 2059 tubes
   Inoculate with 1 µl packaged phage
   Incubate 37°C., 15 minutes
   Add about 3 ml 48° C. top agar
   [50 ml stock containing 150 µl IPTG (0.5M) and 300 µl
   X-GAL (350 mg/ml)]
   Plate on 100mm plates and incubate 37° C., overnight.
4. Efficiency results:

| 4. Efficiency results: | |
|---|---|
| gt11: | 1.7 × 10$^4$ recombinants with 95% background |
| ZAP ® II: | 4.2 × 10$^4$ recombinants with 66% background |

Contaminants in the DNA sample may have inhibited the enzymatic reactions, though the sucrose gradient and organic extractions may have removed them. Since the DNA sample was precious, an effort was made to "fix" the ends for cloning:

Re-Blunt DNA

1. Pool all left over DNA that was not ligated to the lambda arms (Fractions 1–7) and add H$_2$O to a final volume of 12 µl. Then add:

| 143 µl | H$_2$O |
|---|---|
| 20 µl | 10× Buffer 2 (from Stratagene's cDNA Synthesis Kit) |
| 23 µl | Blunting dNTP (from Stratagene's cDNA Synthesis Kit) |
| 2.0 µl | Pfu (from Stratagene's cDNA Synthesis Kit) |

2. Incubate 72° C., 30 minutes.
3. Phenol/chloroform extract once.
4. Chloroform extract once.
5. Add 20 µL 3M NaOAc and 400 µl ice cold ethanol to precipitate.
6. Place at –20° C., overnight.
7. Spin in microfuge, high speed, 30 minutes.
8. Wash with 1 ml 70% ethanol.
9. Spin in microfuge, high speed, 10 minutes and dry.
(Do NOT Methylate DNA Since it was Already Methylated in the First Round of Processing)

Adaptor Ligation

1. Gently resuspend DNA in 8 µl EcoR I adaptors (from Stratagene's cDNA Synthesis Kit).
2. Add:

| 1.0 µl | 10× Ligation Buffer |
|---|---|
| 1.0 µl | 10 mM rATP |
| 1.0 µl | T4 DNA Ligase (4 Wu/µl) |

3. Incubate 4° C., 2 days.
(Do NOT Cutback Since Using ADAPTORS This Time. Instead, Need to Phosphorylate)
Phosphorylate Adaptors 1. Heat kill ligation reaction 70° C., 30 minutes.

| 1.0 µl | 10× Ligation Buffer |
|---|---|
| 2.0 µl | 10 mM rATF |
| 6.0 µl | H$_2$O |
| 1.0 µl | PNK (from Stratagene's cDNA Synthesis Kit). |

3. Incubate 37° C., 30 minutes.
4. Add 31 µl H$_2$O and 5 µl 10X STE.
5. Size fractionate on a Sephacryl S-500 spin column (pool fractions 1–3).
6. Phenol/chloroform extract once.
7. Chloroform extract once.
8. Add ice cold ethanol to precipitate.
9. Place on ice, 10 minutes.
10. Spin in microfuge, high speed, 30 minutes.
11. Wash with 1 ml 70% ethanol.
12. Spin in microfuge, high speed, 10 minutes and dry.
13. Resuspend in 10.5 µl TE buffer.
Do Not Plate Assay. Instead, Ligate Directly to Arms as Above Except Use 2.5 µl of DNA and no Water.
Package and Titer as Above.
Efficiency results:

| gt11: | 2.5 × 10$^6$ recombinants with 2.5% background |
|---|---|
| ZAP II: | 9.6 × 10$^5$ recombinants with 0% background |

Amplification of Libraries (5.0×10$^5$ Recombinants from Each Library)

1. Add 3.0 ml host cells:.(OD$_{600}$=1.0) to two 50 ml conical tube.
2. Inoculate with 2.5×10$^5$ pfu per conical tube.
3. Incubate 37° C., 20 minutes.
4. Add top agar to each tube to a final volume of 45 ml.
5. Plate the tube across five 150 mm plates.
6. Incubate 37° C., 6–8 hours or until plaques are about pin-head in size.
7. Overlay with 8–10 ml SM Buffer and place at 4° C. overnight (with gentle rocking if possible).

Harvest Phage

1. Recover phage suspension by pouring the SM buffer off each plate into a 50-ml conical tube.
2. Add 3 ml chloroform, shake vigorously and incubate at room temperature, 15 minutes.
3. Centrifuge at 2K rpm 10 minutes to remove cell debris.

4. Pour supernatant into a sterile flask, add 500 μl chloroform.
5. Store at 4° C.

Titer Amplified Library

1. Make serial dilutions: $10^{-5}$=1 μl amplified phage in 1 ml SM Buffer $10^{-6}$=1 μl of the $10^{-3}$ dilution in 1 ml SM Buffer
2. Add 200 μl host (in 10 mM MgSO$_4$) to two tubes.
3. Inoculate one with 10 μl $10^{-6}$ dilution ($10^{-5}$).
4. Inoculate the other with 1 μl $10^{-6}$ dilution ($10^{-6}$).
5. Incubate 37° C., 15 minutes.
6. Add about 3 ml 48° C. top agar. [50 ml stock containing 150 μl IPTG (0.5M) and 375 μl X-GAL (350 mg/ml)]
7. Plate on 100 mm plates and incubate 37° C., overnight.
8. Results:

| 8. Results: | |
|---|---|
| gt11: | $1.7 \times 10^{11}$/ml |
| ZAP® II | $2.0 \times 10^{10}$ml |

EXAMPLE 2

Enzymatic Activity Assay

The following is a representative example of a procedure for screening an expression library, prepared in accordance with Example 1, for hydrolase activity.

Plates of the library prepared as described in Example 1 are used to multiply inoculate a single plate containing 200 μL of LB Amp/Meth, glycerol in each well. This step is preformed using High Density Replicating Tool (HDRT) of the Beckman BIOMEK® with a 1% bleach, water, isopropanol, air-dry sterilization cycle between each inoculation. The single plate is grown for 2 h at 37° C. and is then used to inoculate two white 96-well DYNATECH® microliter daughter plates containing 250 μL of LB Amp/Meth, glycerol in each well. The original single plate is incubated at 37° C. for 18 h, then stored at −80° C. The two condensed daughter plates are incubated at 37° C. also for 18 h. The condensed daughter plates are then heated at 70° C. for 45 min. to kill the cells and inactivate the host E. coli enzymes. A stock solution of 5 mg/mL morphourea phenylalanyl-7-amino-4-trifluoromethyl coumarin (MuPheAFC, the 'substrate') in DMSO is diluted to 600 μM with 50 mM pH 7.5 Hepes buffer containing 0.6 mg/mL of the detergent dodecyl maltoside.

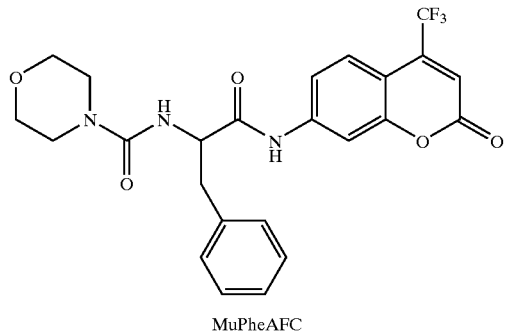

MuPheAFC

Fifty μL of the 600 μM MuPheAFC solution is added to each of the wells of the white condensed plates with one 100 μL mix cycle using the BIOMEK® to yield a final concentration of substrate of ~100 μM. The fluorescence values are recorded (excitation ~400 nm, emission ~505 nm) on a plate reading flurometer immediately after addition of the substrate (t=0). The plate is incubated at 70° C. for 100 min, then allowed to cool to ambient temperature for 15 additional minutes. The fluorescence values are recorded again (t=100). The values at t=0 are subtracted from the values at t=100 to determine if an active clone is present.

The data will indicate whether one of the clones in a particular well is hydrolyzing the substrate. In order to determine the individual clone which carries the activity, the source library plates are thawed and the individual clones are used to singly inoculate a new plate containing LB Amp/Meth, glycerol. As above, the plate is incubated at 37° C. to grow the cells, heated at 70° C. to inactivate the host enzymes, and 50 μL of 600 μM MuPheAFC is added using BIOMEK®.

After addition of the substrate the t=0 fluorescence values are recorded, the plate is incubated at 70° C., and the t=100 min. values are recorded as above. These data indicate which plate the active clone is in.

The enantioselectivity value, E, for the substrate is determined according to the equation below:

$$E = \frac{\ln[(1 - c(1 + ee_p)]}{\ln[(1 - c(1 - ee_p)]}$$

where $ee_p$=the enantiomeric excess (ee) of the hydrolyzed product and c=the percent conversion of the reaction. See Wong and Whitesides, Enzymes in Synthetic Organic Chemistry, 1994, Elsevier, Tarrytown, N.Y. pp. 9–12.

The enantiomeric excess is determined by either chiral high performance liquid chromatography (HPLC) or chiral capillary electrophoresis (CE). Assays are performed as follows: two hundred μL of the appropriate buffer is added to each well of a 96-well white microtiter plate, followed by 50 μL of partially or completely purified enzyme solution; 50 μL of substrate is added and the increase in fluorescence monitored versus time until 50% of the substrate is consumed or the reaction stops, whichever comes first.

EXAMPLE 3

Directed Mutagenesis of Positive Enzyme Activity Clones

Directed mutagenesis was performed on two different enzymes (alkaline phosphatase and 6-glycosidase), using the two different strategies described here, to generate new enzymes which exhibit a higher degree of activity than the wild-type enzymes.

Alkaline Phosphatase

The XL1-Red strain (Stratagene) was transformed with genomic clone 27a3a (in plasmid pBluescript) encoding the alkaline phosphatase gene from the organism OC9a according to the manufacturer's protocol. A 5 ml culture of LB+0.1 mg/ml ampicillin was inoculated with 200 μl of the transformation. The culture was allowed to grow at 37° C. for 30 hours. A miniprep was then performed on the culture, and screening was performed by transforming 2 μl of the resulting DNA into XL-1 Blue cells (Stratagene) according to the manufacturer's protocol and following procedure outlined below (after "Transform XL1 Blue cells). The mutated OC9a phosphatase took 10 minutes to develop color and the wild type enzyme took 30 minutes to develop color in the screening assay.

Standard Alkaline Phosphatase Screening Assay

Transform XL1 Red strain→Inoculate 5 ml LB/amp culture with 200 µl transformation and incubate at 37° C. for 30 hours→Miniprep DNA→Transform XL1 Blue cells→Plate on LB/amp plates→Lift colonies with Duralon UV (Stratagene) or HATF (Millipore) membranes→Lyse in chloroform vapors for 30 seconds→Heat kill for 30 minutes at 85° C.→Develop filter at room temperature in BCIP buffer→Watch as filter develops and identify and pick fastest developing colonies ("positives")→Restreak "positives" onto a BCIP plate BCIP Buffer:

20mm CAPS pH 9.0

1 mm $MgCl_2$ 0.01 mm $ZnCl_2$ 0.1 mg/ml BCIP

Beta-Glycosidase

This protocol was used to mutagenize Thermococcus 9N2 Beta-Glycosidase.

PCR Reaction 2 microliters dNTP's (10 mM Stocks)

10 microliters 10×PCR Buffer 0.5 microliters Vector DNA-31 G1A-100 nanograms 20 microliters 3' Primer (100 pmol)

20 microliters 5' Primer (100 pmol)

16 microliters MnCl $4H_2O$ (1.25 mM Stock)

24.5 microliters $H_2O$ 1 microliter Taq Polymerase (5.0 Units)

100 microliters total

Reaction Cycle

95° C. 15 seconds

58° C. 30 seconds

72° C. 90 Seconds 25 cycles (10 minute extension at 72° C.–4° C. incubation)

Run 5 microliters on a 1% agarose gel to check the reaction.

Purify on a quick QIAQUICK® column (Qiagen).

Resuspend in 50 microliters $H_2O$.

Restriction Digest 25 microliters purified PCR product 10 microliters NEB Buffer #2

3 microliters Kpn I (10 U/microliter)

3 microliters EcoR1 (20 U/microliter)

59 microliters $H_2O$

Cut for 2 hours at 37° C.

Purify on a QIAQUICK® column (Qiagen).

Elute with 35 microliters $H_2O$.

Ligation 10 microliters Digested PCR product 5 microliters Vector (cut with EcoRI/KpnI and phosphatased with shrimp alkaline phosphatase 4 microliters 5× Ligation Buffer 1 microliter T4 DNA Ligase (BRL)

Ligate overnight.

Transform into M15pREP4 cells using electroporation.

Plate 100 or 200 microliters onto LB amp meth kan plates, grow overnight at 37 degrees celsius.

Beta-Glycosidase Assay

Perform glycosidase assay to screen for mutants as follows. The filter assay uses buffer Z (see recipe below) containing 1 mg/ml of the substrate 5-bromo-4-chloro-3-indolyl-6-o-glucopyranoside (XGLU) (Diagnostic Chemicals Limited or Sigma).

Z-Buffer: (referenced in Miller, J. H. (1992) A Short Course in Bacterial Genetics, p. 445.) per liter:

| | |
|---|---|
| $Na_2HPO_4$-$7H_2O$ | 16.1 g |
| $NaH_2PO_4$-$H_2O$ | 5.5 g |
| KCl | 0.75 g |
| $MgSO_4$-$7H_2O$ | 0.246 g |
| 6-mercaptoethanol | 2.7 ml |
| Adjust pH to 7.0 | |

(1) Perform colony lifts using Millipore HATF membrane filters.

(2) Lyse colonies with chloroform vapor in 150 mm glass petri dishes.

(3) Transfer filters to 100 mm glass petri dishes containing a piece of Whatman 3MM filter paper saturated with Z buffer containing 1 mg/ml XGLU. After transferring filter bearing lysed colonies to the glass petri dish, maintain dish at room temperature.

(4) "Positives" were observed as blue spots on the filter membranes ("positives" are spots which appear early). Use the following filter rescue technique to retrieve plasmid from lysed positive colony. Use pasteur pipette (or glass capillary tube) to core blue spots on the filter membrane. Place the small filter disk in an Epp tube containing 20 µl water. Incubate the Epp tube at 75° C. for 5 minutes followed by vortexing to elute plasmid DNA off filter. Transform this DNA into electrocompetent E. coli cells. Repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert.

EXAMPLE 4

Construction of a Stable, Large Insert DNA Library of Picoplankton Genomic DNA

Cell collection and preparation of DNA. Agarose plugs containing concentrated picoplankton cells were prepared from samples collected on an oceanographic cruise from Newport, Oreg. to Honolulu, Hi. Seawater (30 liters) was collected in Niskin bottles, screened through 10 µm Nitex, and concentrated by hollow fiber filtration (Amicon DC10) through 30,000 MW cutoff polyfulfone filters. The concentrated bacterioplankton cells were collected on a 0.22 µm, 47 mm Durapore filter, and resuspended in 1 ml of 2× STE buffer (1M NaCl, 0.1M EDTA, 10 mM Tris, pH 8.0) to a final density of approximately $1 \times 10^{10}$ cells per ml. The cell suspension was mixed with one volume of 1% molten Seaplaque LMP agarose (FMC) cooled to 40° C., and then immediately drawn into a 1 ml syringe. The syringe was sealed with parafilm and placed on ice for 10 min. The cell-containing agarose plug was extruded into 10 ml of Lysis Buffer (10mM Tris pH 8.0, 50 mM NaCl, 0.1M EDTA, 1% Sarkosyl, 0.2% sodium deoxycholate, 1 mg/ml lysozyme) and incubated at 37° C. for one hour. The agarose plug was then transferred to 40 mls of ESP Buffer (1%

Sarkosyl, 1 mg/ml proteinase K, in 0.5M EDTA), and incubated at 55° C. for 16 hours. The solution was decanted and replaced with fresh ESP Buffer, and incubated at 55° C. for an additional hour. The agarose plugs were then placed in 50 mM EDTA and stored at 4° C. shipboard for the duration of the oceanographic cruise.

One slice of an agarose plug (72 µl) prepared from a sample collected off the Oregon coast was dialyzed overnight at 4° C. against 1 mL of buffer A (100 mM NaCl, 10 mM Bis Tris Propane-HCl, 100 µg/ml acetylated BSA: pH 7.0 @ 25° C.) in a 2 mL microcentrifuge tube. The solution was replaced with 250 µl of fresh buffer A containing 10 mM $MgCl_2$ and 1 mM DTT and incubated on a rocking platform for 1 hr at room temperature. The solution was then changed to 250 µl of the same buffer containing 4U of Sau3A1 (NEB), equilibrated to 37° C. in a water bath, and then incubated on a rocking platform in a 37° C. incubator for 45 min. The plug was transferred to a 1.5 ml microcentrifuge tube and incubated at 68° C. for 30 min to inactivate the enzyme and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 ng/µl for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in (this assemblage comprised approximately 4.7% of the total picoplankton biomass (this sample corresponds to "PACI"-200 m in Table 1 of DeLong el al., high abundance of Archaea in Antarctic marine picoplankton, Nature, 371:695–698, 1994). Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^5$ cells, therefore approximately $5.4 \times 10^5$ cells were present in the 72 µl slice used in the preparation of the partially digested DNA.

Vector arms were prepared from pFOS1 as described (Kim el al, Stable propagation of casmid sized human DNA inserts in an F factor based vector, Nucl. Acids Res., 20:10832–10835, 1992). Briefly, the plasmid was completely digested with AstII, dephosphorylated with HK phosphatase, and then digested with Bamli to generate two arms, each of which contained a cos site in the proper orientation for cloning and packaging ligated DNA between 35–45 kbp. The partially digested picoplankton DNA was ligated overnight to the PFOS1 arms in a 15 µl ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to E. coli strain DH10B (BRL), and the cells spread onto $LB_{cm15}$ plates. The resultant fosmid clones were picked into 9-well microliter dishes containing $LB_{cm15}$ supplemented with 7% glycerol. Recombinant fosmids, each containing ca. 40 kb of picoplankton DNA insert, yielded a library of 3.552 fosmid clones, containing approximately $1.4 \times 10^8$ base pairs of cloned DNA. All of the clones examined contained inserts ranging from 38 to 42 kbp. This library was stored frozen at –80° C. for later analysis.

Numerous modifications and variations of the present invention are possible in light of the above teachings; therefore, within the scope of the claims, the invention may be practiced other than as particularly described.

What is claimed is:

1. A method for identifying a protein having a desired activity, the method comprising:

(a) constructing a DNA library from unselected DNA molecules obtained directly from an environmental source;

(b) subjecting the library to mutagenesis (c) expressing the DNA molecules of the mutagenized library to produce proteins; and (d) screening the proteins produced in (c) to identify one or more protein(s) with the desired activity.

2. The method of claim 1, wherein the DNA molecules comprise genomic DNA.

3. The method of claim 2, wherein the genomic DNA is at least about 38 kilobases to about 42 kilobases in length.

4. The method of claim 2, wherein the genomic DNA is at least about 40 kilobases in length.

5. The method of claim 1, wherein at least one of the DNA molecules comprises more than one open reading frame.

6. The method of claim 1, wherein the desired activity is an enzymatic activity.

7. The method of claim 6, wherein the enzymatic activity is hydrolase activity.

8. The method of claim 6, wherein the enzymatic activity is alkaline phosphatase activity.

9. The method of claim 6, wherein the enzymatic activity is beta-glycosidase activity.

10. The method of claim 6, wherein the enzymatic activity is a polyketide synthetase activity.

11. The method of claim 5, wherein the more than one open reading frames encode a complete metabolic pathway or a partial metabolic pathway.

12. The method of claim 1, wherein each member of the library comprises a vector.

13. The method of claim 12, wherein the vector comprises a viral particle, a baculovirus, a phage, a plasmid, a phagemid, a cosmid, a plasmid comprising a fertility (f)-factor (fosmid), a bacterial artificial chromosome, a viral DNA, or any combination thereof.

14. The method of claim 12, wherein the vector comprises chromosomal DNA, non-chromosomal DNA or synthetic DNA.

15. The method of claim 12, wherein the vector further comprises a regulatory sequence for effecting expression of at least a portion of the DNA molecule.

16. The method of claim 1, wherein the environmental source comprises a sample obtained from an arctic location, an antarctic location, a volcanic location or a tropical location.

17. The method of claim 1, wherein the environmental source comprises a sample of soil, water, permafrost, or plant material.

18. The method of claim 1, further comprising producing the identified one or more proteins of (d).

19. The method of claim 1, wherein the screening comprises hybridization screening.

20. The method of claim 1, wherein the screening comprises screening for the presence or absence of a reaction product.

21. The method of claim 1, wherein the screening comprises screening for an enzymatic activity.

* * * * *